US006534980B2

United States Patent
Toufaily et al.

(10) Patent No.: US 6,534,980 B2
(45) Date of Patent: Mar. 18, 2003

(54) DOWNHOLE NMR TOOL ANTENNA DESIGN

(75) Inventors: Ali K. Toufaily, Richmond, TX (US); Abdurrahman Sezginer, Houston, TX (US); Bruno Jorion, Houston, TX (US); Luis E. Depavia, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 09/995,908

(22) Filed: Nov. 28, 2001

(65) Prior Publication Data

US 2002/0033699 A1 Mar. 21, 2002

Related U.S. Application Data

(60) Division of application No. 09/427,370, filed on Oct. 26, 1999, which is a continuation-in-part of application No. 09/368,341, filed on Aug. 9, 1999, now Pat. No. 6,255,818.
(60) Provisional application No. 60/107,184, filed on Nov. 5, 1998.

(51) Int. Cl.[7] .................................................. G01V 3/00
(52) U.S. Cl. ........................................ 324/303; 324/318
(58) Field of Search ................................. 324/303, 300, 324/318, 322, 306, 307, 309, 312, 314

(56) References Cited

U.S. PATENT DOCUMENTS

| 6,008,646 | A | * | 12/1999 | Griffin et al. | ................ 324/303 |
| 6,118,272 | A | * | 9/2000 | Taicher et al. | ............... 324/303 |
| 6,140,817 | A | * | 10/2000 | Flaum et al. | ................ 324/300 |
| 6,348,792 | B1 | * | 2/2002 | Beard et al. | ................. 324/300 |

* cited by examiner

Primary Examiner—Louis Arana
(74) Attorney, Agent, or Firm—Brigitte L. Jeffery; Kevin P. McEnancy

(57) ABSTRACT

An NMR tool includes RF antennae and a cylindrical permanent magnet to establish a static magnetic $B_0$ field for performing the NMR measurement sequence. The magnetic field of the magnet is polarized across the diameter of the magnet. A ferrite material is located adjacent to the permanent magnet. The antennae are located near opposite ends of the ferrite material and are formed from corresponding coils that are wound around the ferrite material such that the magnetic moments of the antennae are parallel to the longitudinal axis of the magnet.

36 Claims, 12 Drawing Sheets

|  | State 1 | State 2 | State 3 | State 4 |
|---|---|---|---|---|
| Output | 1111 1110 | 0001 1000 | 1101 0001 | 0000 0000 |
| Duration | 500 us | 200 us | 450 us | 100 us |
| Looping |  | 3*{ | } |  |

FIG. 6

| Data Block | Function | Component |
|---|---|---|
| 1 | Number of States | Single Number |
| 2 | State 1 Descriptor | Output Duration Next State Loop Count |
| ⋮ | ⋮ | ⋮ |
| n | State n Descriptor | Output Duration Next State Loop Count |

FIG. 8

|  | 1 | 2 | 3 | 4 | 5 | 6 | 7 | 8 | 9 | 10 | 11 |
|---|---|---|---|---|---|---|---|---|---|---|---|
| Title | Delay | Pi/2 | Q Sw | Delay | Delay | Pi | Q Sw | Delay | Acq | Delay | End |
| Duration | 10 ms | 16 us | 20 us | 107 us | 50 us | 30 us | 30 us | 75 us | 300 us | 25 us | 10 us |
| Loop | 8{..} | | | | 1200{..} | | | | | ..} | ..} |
| RF | | | | | | -Y | | | | | |
| TX Phase | T1/11 | | | | | | | | | | |
| BS | | | | | | | | | | | |
| RX | | | | | | | | | | | |
| BL | T1/11 | | | | | | | | | | |
| ACQ | | | | | | | | | | | |
| FREQ | T1/11 | | | | | | | | | | |
| End of CPMG | | | | | | | | | | | |

FIG. 7

| Data Block | Function | Component |
|---|---|---|
| 1 | Number of States | 4 |
| 2 | State 1 Descriptor | Output 1111 1110<br>Duration 500 us<br>Jump to (If Loop Count is NOT Zero): Not Applicable<br>Loop Count: 0 |
| 3 | State 2 Descriptor | Output 0001 1000<br>Duration 200 us<br>Jump to (If Loop Count is NOT Zero): Not Applicable<br>Loop Count: 0 |
| 4 | State 3 Descriptor | Output 1101 0001<br>Duration 450 us<br>Jump to (If Loop Count is NOT Zero): State 2<br>Loop Count: 3 |
| 2 | State 1 Descriptor | Output 0000 0000<br>Duration 100 us<br>Jump to (If Loop Count is NOT Zero): Not Applicable<br>Loop Count: 0 |

FIG. 8A

| | Duration | Output |
|---|---|---|
| 372 | 500 us | 1111 1110 |
| 372 | 200 us | 0001 1000 |
| 372 | 450 us | 1101 0001 |
| 372 | 200 us | 0001 1000 |
| 372 | 450 us | 1101 0001 |
| 372 | 200 us | 0001 1000 |
| 372 | 450 us | 1101 0001 |
| 372 | 100 us | 0000 0000 |

DOWNHOLE NMR TOOL ANTENNA DESIGN

CROSS REFERENCE TO RELATED APPLICATIONS

This application is a divisional of U. S. patent application Ser. No. 09/427,370, filed Oct. 26, 1999, which is a continuation-in-part to U.S. patent application Ser. No. 09/368,341, entitled, "Method and Apparatus for Performing Magnetic Resonance Measurements," filed on Aug. 9, 1999, now U.S. Pat. No. 6,255,818 issued Jul. 3, 2001 which claims the benefit of provisional application No. 60/107,184 filed Nov. 5, 1998.

BACKGROUND

Nuclear magnetic resonance (NMR) measurements typically are performed to investigate properties of a sample. For example, an NMR wireline or logging while drilling (LWD) downhole tool may be used to measure properties of subterranean formations. In this manner, the typical downhole NMR tool may, for example, provide a lithology-independent measurement of the porosity of a particular formation by determining the total amount of hydrogen present in fluids of the formation. Equally important, the NMR tool may also provide measurements that indicate the dynamic properties and environment of the fluids, as these factors may be related to petrophysically important parameters. For example, the NMR measurements may provide information that may be used to derive the permeability of the formation and viscosity of fluids contained within the pore space of the formation. It may be difficult or impossible to derive this information from other conventional logging arrangements. Thus, it is the capacity of the NMR tool to perform these measurements that makes it particularly attractive versus other types of downhole tools.

Typical NMR logging tools include a magnet that is used to polarize hydrogen nuclei (protons) in the formation and a transmitter coil, or antenna, that receives radio frequency (RF) pulses from a pulse generator of the tool and in response, radiates RF pulses into the formation. A receiver antenna may measure the response (indicated by a received RF signal called a spin echo signal) of the polarized hydrogen to the transmitted pulses. Quite often, the transmitter and receiver antennae are combined into a single transmitter/receiver antenna.

The NMR techniques employed in current NMR tools typically involve some variant of a basic two step technique that includes delaying for a polarization time and thereafter using an acquisition sequence. During the polarization time (often referred to as a "wait time"), the protons in the formation polarize in the direction of a static magnetic field (called $B_0$) that is established by a permanent magnet (of the NMR tool).

An example of an NMR sequence is a Carr-Purcell-Meiboom-Gill (CPMG) sequence 15 that is depicted in FIG. 1. By applying the sequence 15, a distribution of spin relaxation times (T2 times, for example) may be obtained, and this distribution may be used to determine and map the properties of a formation. A technique that uses CPMG sequences 15 to measure the T2 times may include the following steps. In the first step, the NMR tool pulses an RF field (called the $B_1$ field) for an appropriate time interval to apply a 90° excitation pulse 14a to rotate the spins of hydrogen nuclei that are initially aligned along the direction of the $B_0$ field. Although not shown in detail, each pulse is effectively an envelope, or burst, of an RF carrier signal. When the spins are rotated around $B_1$ away from the direction of the $B_0$ field, the spins immediately begin to precess around $B_0$. At the end of the pulse 14a, the spins are rotated by 90° into the plane perpendicular to the $B_0$ field. The spins continue to precess in this plane first in unison, then gradually losing synchronization.

For step two, at a fixed time $T_{CP}$ following the excitation pulse 14a, the NMR tool pulses the $B_1$ field for a longer period of time (than the excitation pulse 14a) to apply an NMR refocusing pulse 14b to rotate the precessing spins through an angle of 180° with the carrier phase shifted by ±90°. The NMR pulse 14b causes the spins to resynchronize and radiate an associated spin echo signal 16 (see FIG. 2) that peaks at $2.T_{CP}$ after the 90° tipping pulse 14a. Step two may be repeated "k" times (where "k" is called the number of echoes and may assume a value anywhere from several to as many as several thousand, as an example) at the interval of $2.T_{CP}$. For step three, after completing the spin-echo sequence, a waiting period (usually called a wait time) is required to allow the spins to return to equilibrium along the $B_0$ field before starting the next CPMG sequence 15 to collect another set of spin echo signals. The decay of the amplitudes of each set of spin echo signals 16 may be used to derive a distribution of T2 times.

Although it may be desirable to vary the characteristics of the measurement sequence to optimize performance to a particular formation, unfortunately, a conventional NMR tool may be specifically designed to perform a predefined NMR measurement sequence. Thus, the conventional tool may provide limited flexibility for changing the sequence, as the parameters that may be programmed into the tool may affect the global timing of the sequence without allowing the flexibility to change a particular portion of the sequence. For example, a conventional NMR tool may be programmed with the above-described $T_{CP}$ time, the time between the tipping pulse 14a and the first refocusing pulse 14b. However, this value also sets the time ($2.T_{CP}$) between successive refocusing pulses 14b. Thus, although a time between refocusing pulses 14b other than $2.T_{CP}$ may be desired to optimize performance of the tool, the tool may not provide the flexibility to change this time.

SUMMARY OF THE INVENTION

The subject invention is an NMR measurement apparatus comprising a permanent magnet, a ferromagnetic material located adjacent to the permanent magnet, and at least one coil circumscribing the ferromagnetic material. A circuit is coupled to the coil and adapted to use at least one coil and the permanent magnet to perform NMR measurements.

Another embodiment of the invention is an NMR measurement apparatus comprising a permanent magnet, a metallic housing at least partially encasing the permanent magnet, and at least one coil located outside of the housing. A circuit is coupled to the coil and adapted to use at least one coil and the permanent magnet to perform NMR measurements.

BRIEF DESCRIPTION OF THE DRAWING

FIG. 6 is an illustration of state descriptors according to an embodiment of the invention.

FIG. 7 is an illustration of a graphical user interface that may be used to program the tool of FIG. 3 according to an embodiment of the invention.

FIG. 8 is an illustration of the packaging of state descriptors before transmission to the NMR measurement tool according to an embodiment of the invention.

FIG. 8A is an illustration of the packaging of the state descriptors of FIG. 6.

DETAILED DESCRIPTION

Figure 3:
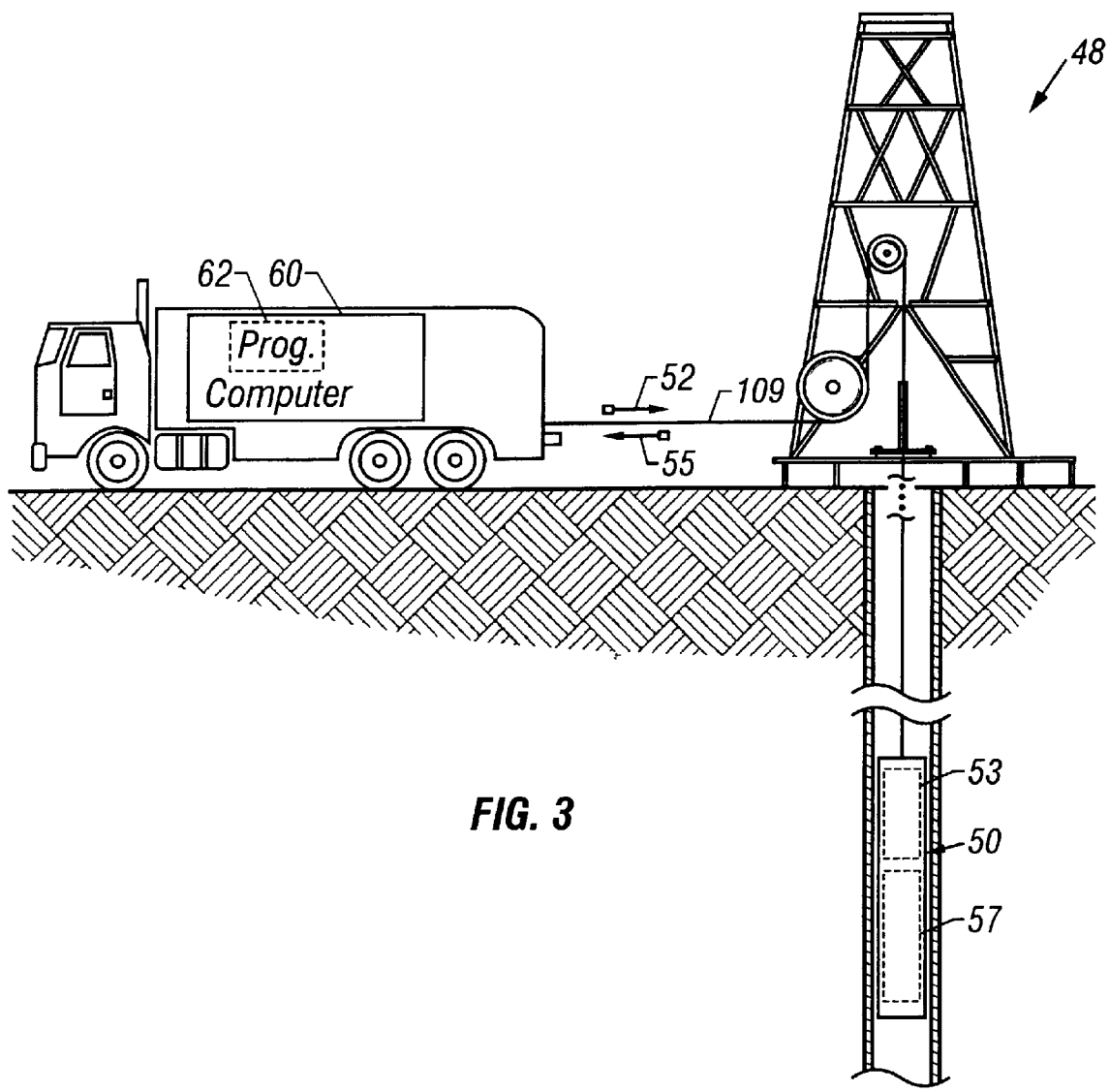
FIG. 3 is a schematic diagram of a system that uses a programmable NMR measurement tool in accordance with an embodiment of the invention.

Referring to FIG. 3, an embodiment 48 of a NMR measurement system in accordance with the invention includes a nuclear magnetic resonance (NMR) wireline tool 50 that may be programmed with a wide range of NMR measurement sequences. In particular, the tool 50 is constructed to receive logging sequence data 52 that defines a particular NMR measurement sequence to be performed by the tool 50. The data 52, in turn, includes state descriptors, each of which indicates a state of the NMR measurement sequence during an associated time slice, or interval, of the sequence. Thus, due to this arrangement, the tool 50 may generate the NMR measurement sequence in response to the state descriptors, as described below. In some embodiments, the state descriptors may be generated by a computer 60 (located at the surface of the well, for example) that communicates the resultant data 52 via a wireline 109 to the tool 50, as described below. The computer 60 may also receive magnetic resonance (MR) data 55 from the tool 50 via the wireline 109. The data 52 may be loaded into the tool 50 via other techniques (via a serial link before the tool 50 is lowered downhole, for example) other than the above-described wireline technique.

Each state descriptor is associated with a particular time interval of the NMR measurement sequence and indicates the logical states of various signals that control the tool 50 during that time interval. For example, a particular state descriptor may indicate the state of a digital signal that establishes the frequency of a carrier signal of transmitted radio frequency (RF) pulses, and the same state descriptor may indicate the state of another digital signal that indicates a phase of the carrier signal, as just a few examples. As another example, a particular state descriptor may indicate the logic levels of voltages that are used to operate switches of the tool 50 to generate the NMR measurement sequence, as described below. In some embodiments, each state descriptor may also indicate the duration of the associated time interval.

The tool 50 may store state descriptors for several NMR measurements. In this manner, the sequence(s) to be used may be selected before the tool 50 is lowered downhole. Furthermore, due to the tool's 50 ability to store state descriptors for multiple NMR measurement sequences, the tool 50 may use different sequences downhole. For example, the tool 50 may use sequences that have different RF frequencies for purposes of establishing different resonance shells 406 (see FIG. 16) to investigate different regions of the formation, as further described below.

The tool 50 includes circuitry 53 that is electrically coupled to an NMR sensor 57 of the tool 50. As described below, the circuitry 53 receives the data 52 from the wireline 109 and interacts with the sensor 57 to perform a given NMR measurement sequence and also communicates the MR data 55 (via the wireline 109) to the computer 60.

Figure 1:
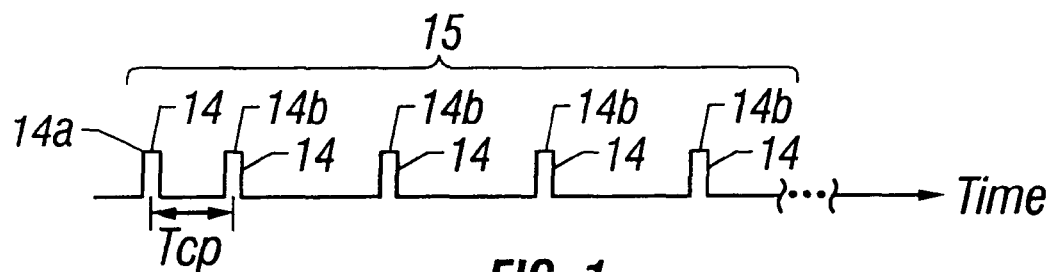
FIG. 1 is an illustration of an NMR measurement sequence according to the prior art.
Figure 2:
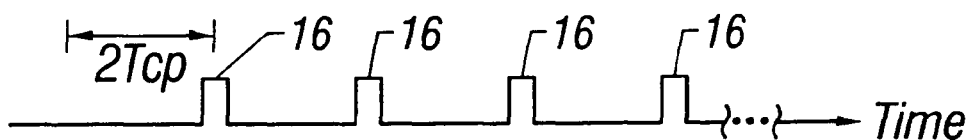
FIG. 2 is an illustration of spin echo signals produced in response to the NMR measurement sequence of FIG. 1.
Figure 4:
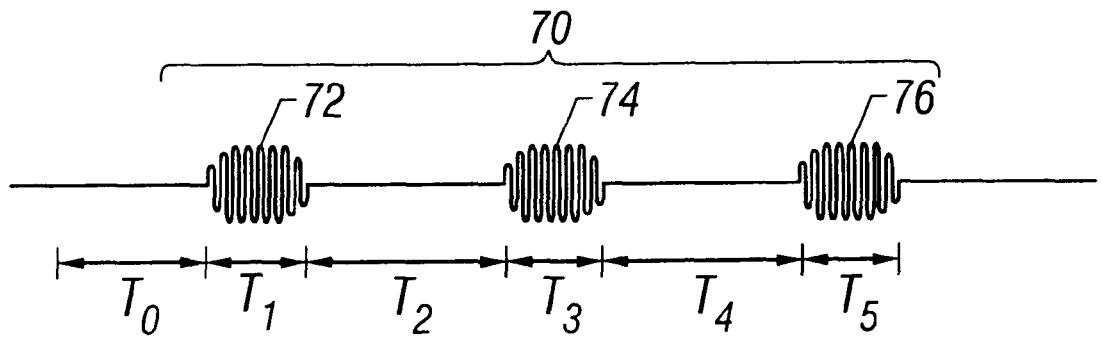
FIG. 4 is an illustration of an exemplary portion of an NMR measurement sequence according to an embodiment of the invention.

Referring to FIG. 4, as an example, an exemplary portion 70 of an NMR measurement sequence may span a duration formed by successive time intervals $t_0$, $t_1$, $t_2$, $t_3$, $t_4$, and $t_5$. Each of these time intervals, in turn, is associated with a state descriptor. For example, during the $t_1$ time interval, the corresponding state descriptor may indicate logical states of signals to cause the transmission of an RF pulse 72 (a tipping pulse or a refocusing pulse, as examples). Furthermore, during the $t_0$ time interval, the state descriptor that is associated with the $t_0$ time interval may indicate signal states that establish a phase and a frequency of the RF carrier signal for the RF pulse 72. As another example, during the $t_1$ time interval, the state descriptor that is associated with the $t_1$ time interval may indicate a switching signal state that causes an input to an RF receiver of the tool 50 to be shorted (to prevent false readings) during the transmission of the RF pulse 72.

Similarly, other state descriptors may indicate the appropriate signal states to cause the generation of other RF pulses (such as the RF pulses 74 and 76) during the exemplary portion 70 of the NMR measurement sequence that is depicted in FIG. 4. As another example, for the case where the RF pulse 72 is a refocusing pulse, the state descriptor that is associated with the time interval $t_2$ may indicate a signal state that causes the transmission antenna (that is used to radiate the RF pulse 72) to be isolated from the receiver circuitry (of the tool 50) during the $t_2$ time interval when a spin echo signal is received. As noted above, besides indicating signal states, in some embodiments, each state descriptor indicates its own duration. Thus, for example, the state descriptor that is associated with the $t_2$ time interval establishes the duration of the $t_2$ time interval.

Figure 5:
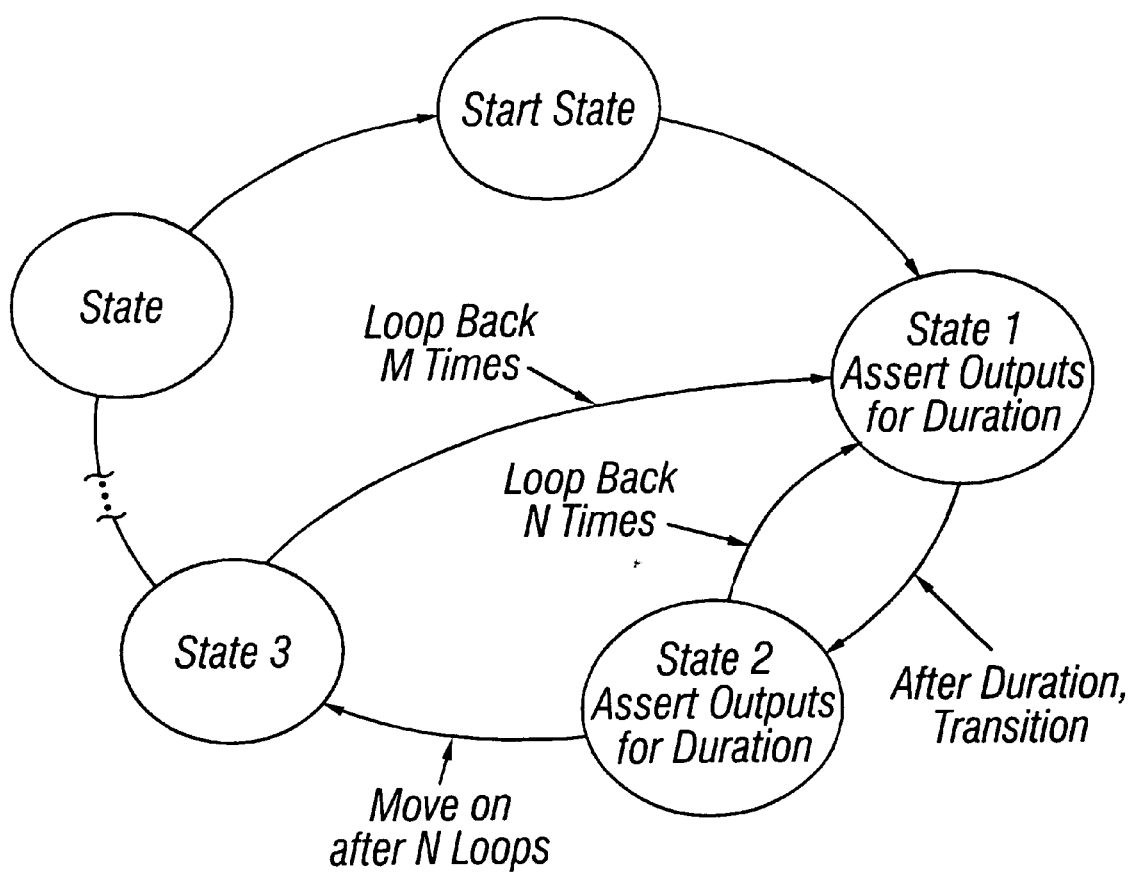
FIG. 5 is a state diagram illustrating states of an NMR measurement sequence according to an embodiment of the invention.

Referring to FIG. 5, thus, each state descriptor is associated with a general state (denoted by "STATE" in the description below) of the NMR measurement sequence. For example, one STATE may occur during the transmission of a refocusing pulse and another STATE may occur during the subsequent time interval when a spin echo signal is received. In this manner, referring to FIG. 5 that depicts an exemplary state diagram for the NMR measurement sequence, in STATE1 of the NMR measurement sequence, the associated state descriptor causes the assertion/deassertion of various signals in the circuitry 53 to control the output of the tool 50 during STATE1 and to possibly establish parameters (such as a carrier phase and a frequency as examples) that are used in an upcoming STATE of the NMR measurement sequence. After the time interval that is associated with STATE1 elapses, the NMR measurement sequence moves to STATE2, a STATE described by another state descriptor. In this manner, the state descriptor that is associated with STATE2 causes the assertion/deassertion of various signals in the circuitry 53.

As depicted in FIG. 5, the NMR measurement sequence may loop between STATE1 and STATE2 N times. To accomplish this, in some embodiments, the state descriptor that is associated with STATE1 indicates the beginning of the loop, and the state descriptor that is associated with STATE2 indicates the end of the loop. Either the state descriptor that described STATE1 or the state descriptor that describes STATE2 may indicate the number of times (N, for this example) to repeat the loop. After N loops, the NMR measurement sequence moves on to STATE3, a state controlled by another state descriptor. As depicted in FIG. 5, another loop (of M times) that includes STATE1, STATE2 and STATE 3 may be created, as another example.

Thus, the state descriptors may be used to control states of the NMR measurement sequence. To summarize, each state descriptor may indicate some or all of the following attributes. First, each state descriptor indicates the states of various signals that are used to establish the associated state or future states of the NMR measurement sequence. The state descriptor may also indicate the duration of the associated NMR measurement sequence state. The state descriptor may also indicate parameters (a carrier frequency or a carrier phase, as examples) of the next NMR measurement sequence state after the current state elapses. Regarding loops, the state descriptor may indicate a beginning of a loop or an end of a loop, and the state descriptor may indicate a repeat count for a loop.

FIG. 6 depicts four exemplary state descriptors 90, 92, 94 and 96, each of which is associated with a different state (called STATE1, STATE2, STATE3 and STATE4 but are not necessarily related to the states that are depicted in FIG. 5) of an NMR measurement sequence. In this manner, the state descriptor 90 (associated with STATE1) indicates the output states (denoted by "11111110b," where the suffix "b" denotes a binary representation) for one or more signals of the tool 50. The state descriptor 90 also indicates a duration of 500 microseconds ($\mu$s) for STATE1 and does not indicate the beginning or end of any loops. Therefore, at the end of 500 $\mu$s, the NMR measurement sequence enters STATE2, a state described by the state descriptor 92. The state descriptor 92 indicates the output states of one of more signals of the tool 50 and also indicates a duration of 200 microseconds ($\mu$s) for STATE2. The state descriptor 92 further indicates the beginning (depicted by "{" in FIG. 6) of a loop that is repeated three times. At the end of 200 $\mu$s, the NMR measurement sequence enters STATE3, a state associated with state descriptor 94, and remains in STATE3 for the indicated duration (450 $\mu$s). The state descriptor 94 indicates the end of the loop that begins with STATE2. Thus, after the 450 $\mu$s duration, the NMR measurement sequence transitions back to STATE2 to traverse the loop again. After the loop is repeated three times, the NMR measurement sequence transitions to STATE4 that is associated with the state descriptor 96 and remains in STATE4 for 100 $\mu$s. Although one loop is described in the above example, the state descriptors may indicate multiple loops, and the state descriptors may indicate nested loops.

Referring to FIG. 7, in some embodiments, the program 62 (see FIG. 3), when executed by the computer 60, causes the computer 60 to form a graphical user interface (GUI) 97 (on a display of the computer 60) that permits visual creation and editing of the states of the NMR measurement sequence. In this manner, the GUI 97 displays columns (columns 1–11, for example, as depicted in FIG. 7), each of which is associated with a state of the NMR measurement sequence. As depicted in FIG. 7, an upper row of the GUI 97 is a title row that permits labeling of each column for ease of reference. In this manner, the states may be titled and re-titled by clicking on the title of a particular state with a mouse and renaming the state by using the keyboard of the computer. The displayed signal states and state durations that are described below may be changed or entered in a similar fashion.

The row below the title row displays the duration of each state, and the row between the displayed state durations displays embedded loop codes. For example, in column 1, the characters "8{" indicate the beginning of an outer loop that is repeated eight times. As example, the outer loop may define eight NMR measurements. In column 5, the characters "1200{" indicate the beginning of an inner nested loop that is repeated 1200 times. As an example, the inner loop may define refocusing pulses and delays to allow spin echo acquisition, and the portion of the outer loop that is outside of the inner loop may define a tipping pulse.

The remaining rows of the GUI 97 indicate logical signal states for each state of the NMR measurement sequence. For example, a signal denoted by "RF" has a logic one level to indicate the beginning of a pulse and has a zero logic level otherwise. As another example, a signal denoted by "ACQ" indicates an acquisition phase with a logic one level and has a logic zero level otherwise. Some of the other signals that are depicted in FIG. 7 are described below in connection with the circuitry 53 of the tool 50.

Referring to FIG. 8, the computer 60 may package the state descriptors in the following manner to form the data 52 that is communicated to the tool 50. The first data block that is communicated to the tool 50 may include header information, such as the number of state descriptors that are being communicated. The subsequent data blocks are formed from the state descriptors in the order of the corresponding states. Thus, the second block of data is the state descriptor for the STATE1, the third block of data is the state descriptor for the STATE2, etc.

FIG. 8A depicts an example of the packaging of the state descriptors 90, 92, 94 and 96 of FIG. 6. As shown, the first data block indicates that the number of states is four. The next four blocks depict the state descriptors 90, 92, 94, 96, respectively. As shown, the state descriptor 92 indicates a loop count of three while the other state descriptors 90, 94 and 96 indicate loop counts of zero. In this manner, each time the state corresponding to the state descriptor 92 occurs, the corresponding loop counter is decremented by one. Also depicted in FIG. 8A are the branch conditions (called "jumps" in FIG. 8A) that indicate the next state. If the loop count is zero, then control transitions to the next successive state. However, if the loop count is not zero, then the corresponding branch condition indicates the next state.

Figure 9:
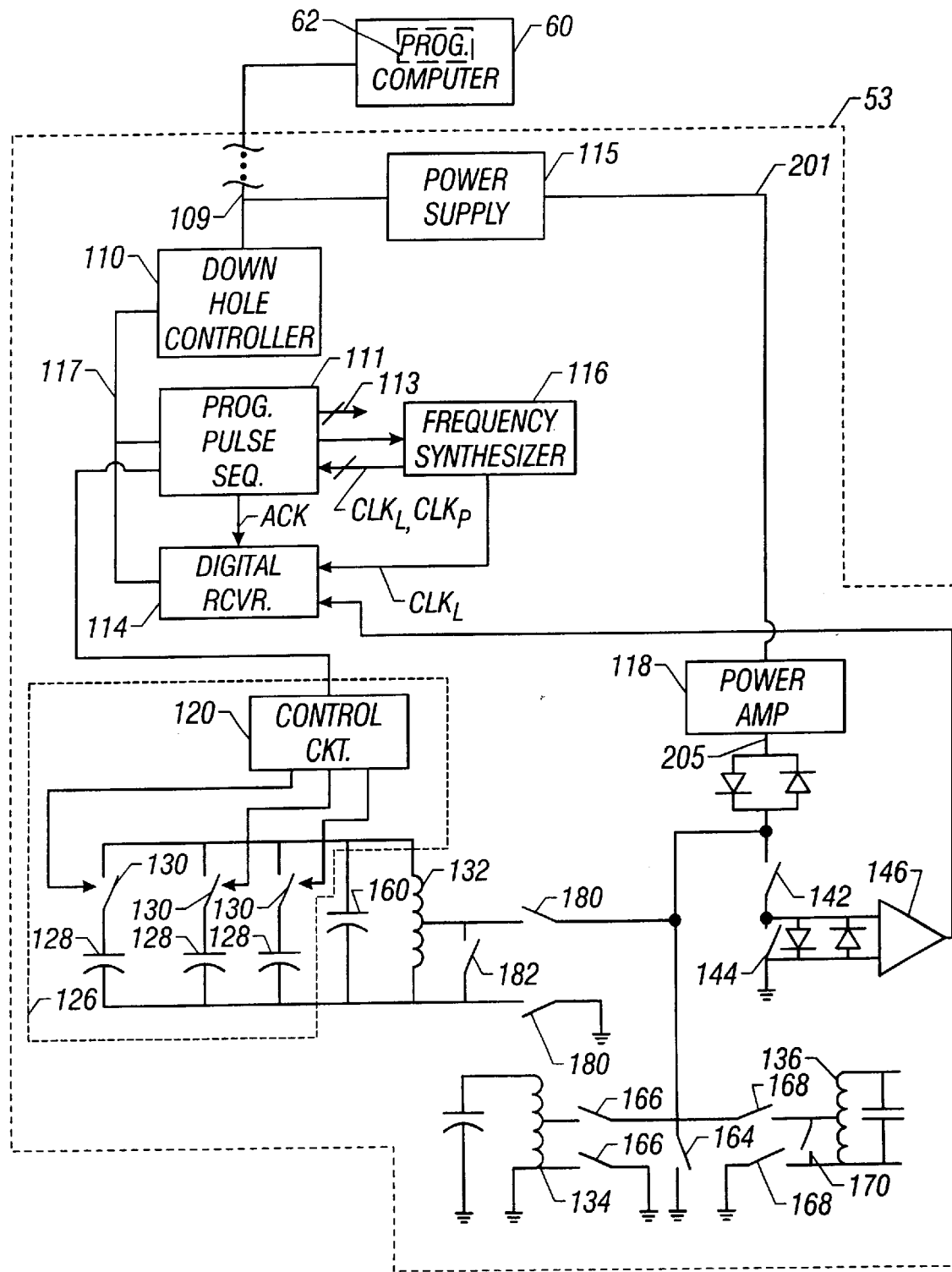
FIG. 9 is a schematic diagram of circuitry of the tool according to an embodiment of the invention.

Referring to FIG. 9, in some embodiments, the circuitry 53 communicates with the computer 60 to perform a given NMR measurement sequence based on the state descriptors. To accomplish this, a downhole controller 110 is coupled to the wireline 109 to communicate with the computer 60 to receive the data 52 and provide the resultant state descriptors to a programmable pulse sequencer 111. The pulse sequencer 111, in turn, executes the state descriptors to generate signals (on signal lines 113) that control the NMR measurement sequence. In the course of the NMR measurement sequence, the pulse sequencer 111 may perform the following actions: generate signals that operate a power amplifier 118 to generate RF transmission pulses, communicate (via a serial bus 121) with a resonance tuning circuit 112 to control the resonance frequency of a main receiving antenna 132 (represented by an inductor), control (via an ACQ signal) the activation of digital receiver circuitry 114, control the activation of transmission circuitry and generate signals to control various switches of the circuitry 53, as further described below.

Besides the pulse sequencer 111, the circuitry 53 includes a frequency synthesizer 116 that is coupled to the pulse sequencer 111 to generate clock signals for the circuitry 53 based on executed state descriptors. For example, the frequency synthesizer 116 may generate clock signals based on the RF frequency and phase that are indicated by an executed state descriptor. The pulse sequencer 111 may then use one of these clock signals to generate an RF transmission pulse by interacting with the power amplifier 118. A bus 117 establishes communication between the digital receiver 114, the downhole controller 110 and the pulse sequencer 111. The circuitry 53 is coupled to multiple antennae 132, 134 and 136 of an NMR sensor 57, described below. The main antenna 132 may be used to transmit RF pulses and receive spin echo signals. In some embodiments, the other antennae 134 and 136 are used to receive spin echo signals. The antennae 132, 134 and 136 are distributed along the length of the sensor 57, an arrangement that may be used to obtain high resolution T1 measurements and multiple T1 measurements using a single NMR measurement sequence, as further described in U.S. Pat. No. 6,255,818 issued Jul. 3, 2001.

The generation of a transmission pulse (a refocusing pulse or a tipping pulse, as examples) may occur in the following manner. First, the pulse sequencer 111 executes a particular state descriptor that indicates (via a signal called RF) that an RF pulse is to be generated during the next NMR measurement state. In this manner, during the next NMR measurement state, the pulse sequencer 111 uses a clock signal that is provided by the frequency synthesizer to generate signals to produce an RF pulse at the output of the power amplifier 118. During the next state, the pulse sequencer 111 executes the next state descriptor that causes the pulse sequencer 111 to activate the appropriate switches to couple the output terminal of the power amplifier 118 to one of the three antennae (the antenna 132, 134 or 136) and isolate the remaining two antennae. The execution of this descriptor also causes the pulse sequencer 111 to assert a signal that activates switch 144 to short out the input terminals of a preamplifier 146 of the receiving circuitry; deassert a signal that deactivates switch 142 to decouple the preamplifier 146 from the output terminal of the power amplifier 118; and deassert the ACQ signal to disable the digital receiver 114 (that receives an output signal from the preamplifier 146), as just a few examples of the signals that may be controlled by a particular state descriptor.

To receive a spin echo signal, the appropriate state descriptor causes the ACQ signal to be asserted to enable the digital receiver 114; causes the BS signal to be deasserted to enable reception of a signal by the preamplifier 146; and causes the assertion/deassertion of the appropriate switches to couple the main antenna 132 to the input terminals of the preamplifier 146 while isolating the remaining antennae 134 and 136 from the rest of the circuitry 53.

If As depicted in FIG. 9, switches 180, switches 168 and switches 166 are controlled via signals that are generated from the execution of the state descriptors to selectively couple the antennae 132, 136 and 134, respectively, to an output terminal of the power amplifier 118. Switches 182, 164 and 170 are controlled via signals that are generated from the execution of the state descriptors to selectively shunt coils of the antennae 132, 134 and 136, respectively, to ground.

Figure 10:
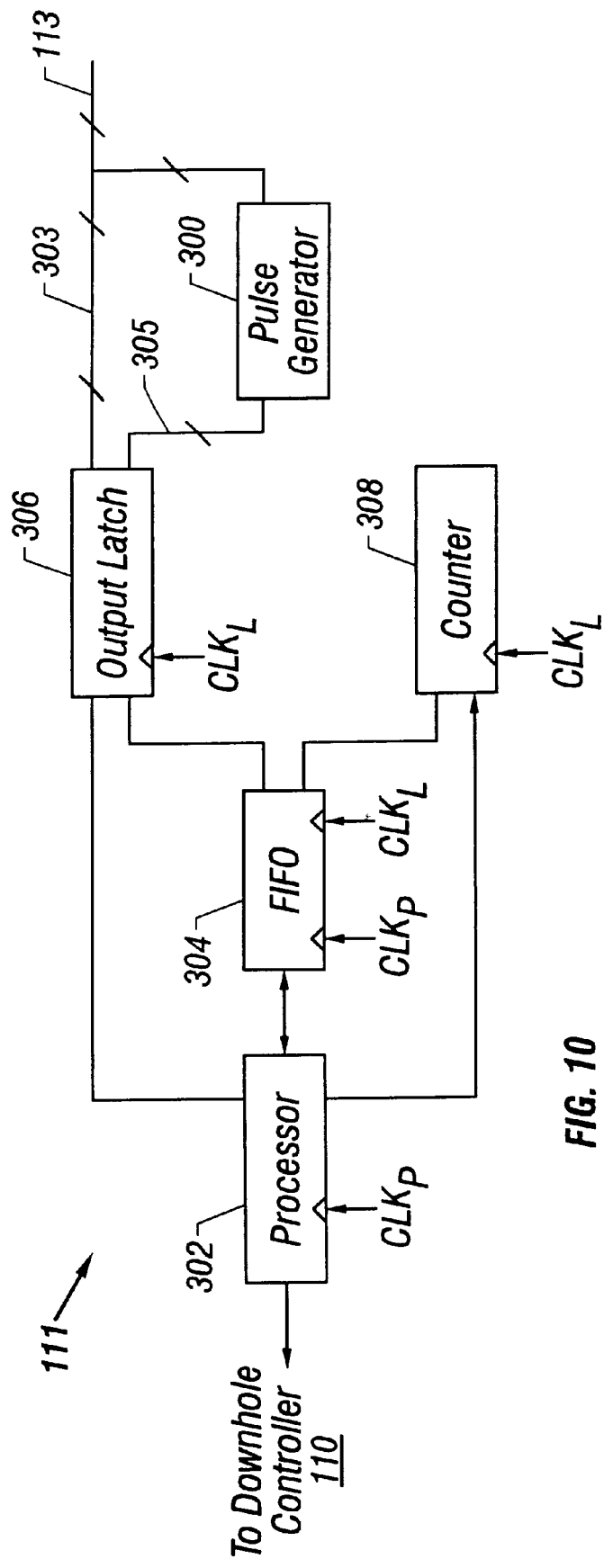
FIG. 10 is a schematic diagram of a pulse sequencer of the tool of FIG. 9 according to an embodiment of the invention.
Figures 11, 11A:
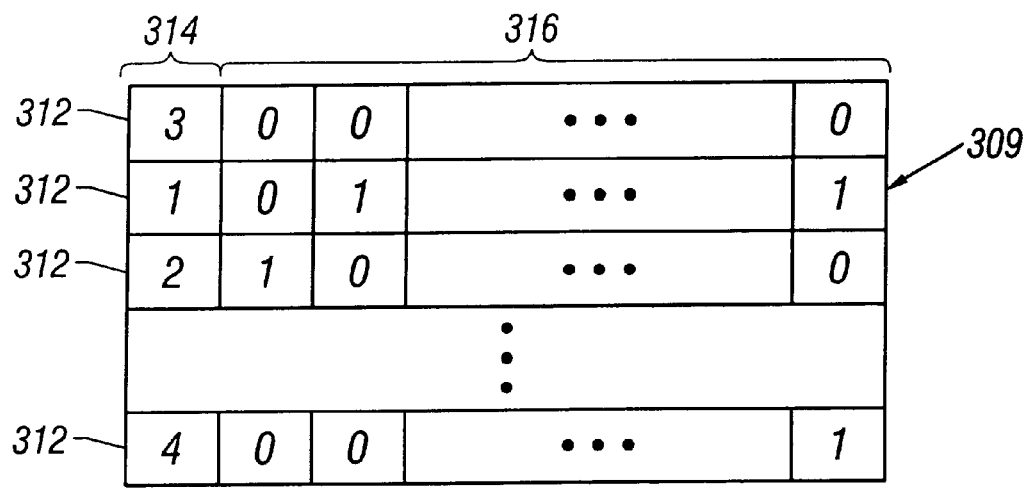
FIG. 11 is an illustration of the organization of data in a memory of the pulse sequencer of FIG. 10 according to an embodiment of the invention.
FIG. 11A is an illustration of the unfolding of the state descriptors to remove loops.

Referring to FIGS. 10 and 11, in some embodiments, the pulse sequencer 111 includes a processor 302 (a digital signal processor (DSP), for example) that communicates with the downhole controller 110 to receive the state descriptors. For purposes of executing the state descriptors, the processor 302 removes any loops, or branches, that exist between the state descriptors to create a linearized pipelined stack 309 of descriptors 312. (see FIG. 11) for execution. For example, the state descriptors that describe STATE1 and STATE2 may form a loop between STATE1 and STATE2 that repeats N times. To remove the branches, the processor 302 creates a stack of 2N descriptors 312.

Each descriptor 312 includes a field 314 that indicates the duration of the associated state of the NMR measurement sequence. For example, the field 314 may indicate the number of clock periods that elapse during the associated state. In some embodiments, each clock period is set approximately equal to one divided by the Larmor frequency. Each descriptor 312 also includes a field 316 that indicates the states of various signals. For example, a particular bit of the field 316 may indicate a logical state of a switching signal. However, groups of bits in the field 316 may collectively indicate a digital signal, such as an RF frequency or phase, for example.

As a more specific example, FIG. 11A depicts the unfolding of the state descriptors 90, 92, 94 and 96 (see FIG. 6) to form eight descriptors 372 that may be successively executed by the processor 302. In this manner, the first descriptor 372 is directly derived from the descriptor 90 and indicates a duration of 500 µs. The next six descriptors 372 are basically three copies of the descriptor 92 (that indicates a duration of 200 µs) followed by the descriptor 94 (that indicates a duration of 450 µs). Finally, the remaining descriptor 372 is directly derived from the descriptor 96 (that indicates a duration of 100 µs).

Referring back to FIG. 10, the processor 302 stores the unfolded state descriptors in a first-in-first-out (FIFO) fashion in a FIFO memory 304. In some embodiments, the FIFO memory 304 may assert a signal to alert the processor 302 when the FIFO memory 304 becomes half empty so that the processor 302 may store additional descriptors in the FIFO memory 304. An output latch 306 of the pulse sequencer 111 receives the bits from the field 316, and a counter 308 of the pulse sequencer 111 receives the bits from field 314. In some embodiments, both the counter 308, the output of the FIFO memory 304 and the latch 306 are clocked by a clock signal (called $CLK_L$) at the Larmor frequency. In some embodiments, the counter 308 is a decrementing counter that signals the processor 302 when its count is zero. In response to this signal, the processor 302 causes the latch 306 and the counter 308 to load new data from the FIFO memory 304. In this manner, for each state descriptor, the output latch 306 provides signals indicative of the field 316 for the number of Larmor clock signals that is indicated by the field 314. Some of these signals are communicated to a pulse generator 300 (via conductive lines 305) and some of the signals are communicated to conductive lines 303 that control the various circuits described above. The pulse generator 300 generates the signals to control the power amplifier 118. The input of the FIFO 304 and the processor 302 are clocked at a higher frequency (via a higher frequency $CLK_p$) than the Larmor frequency. This frequency difference allows more processing time for the processor 302 to process the state descriptors and thus, promotes continuous execution of the state descriptors.

Referring back to FIG. 9, among the other features of the circuitry 53, a resonance tuning circuit 126 may be used to tune the main antenna 132. In this manner, the circuit 126 includes capacitors 128 that may be selectively coupled (via a serially coupled switch 130) in parallel with the main antenna 132. Another capacitor 160 may be permanently coupled in parallel with the main antenna 132 to establish a base resonant frequency for the antenna 132. Due to this arrangement, the downhole controller 110 may selectively activate the switches 128 to adjust the resonance frequency of the main antenna 132. To accomplish this, in some embodiments, the resonance tuning circuit 126 includes a control circuit 120 that is coupled to the serial bus 121. In this manner, the control circuit 120 serves as a bus interface to permit selective activation of the switches 130 by the downhole controller 110.

Figure 12:
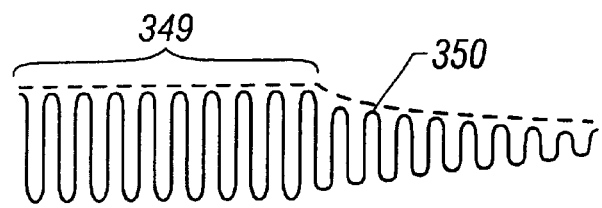
FIG. 12 is a waveform illustrating the decay of a radio frequency (RF) signal that is used to automatically tune the resonant frequency of an antenna of the pulse sequencer according to an embodiment of the invention.
Figure 13:
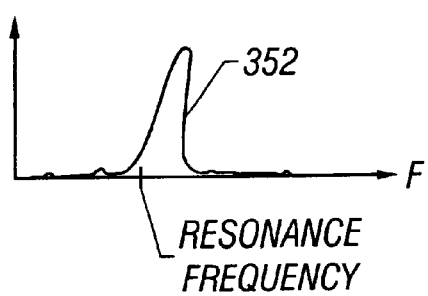
FIG. 13 is a spectral distribution of the signal of FIG. 12.

In some embodiments, the downhole controller 110 automatically tunes the resonance frequency of the antenna 132 after each NMR measurement sequence. In this manner, at the end of the sequence, the downhole controller 110 causes the pulse sequencer 111 to generate a calibration pulse 349 that is depicted in FIG. 12. The downhole controller 110 opens the switch 144 (see FIG. 9) and closes the switch 142 to observe a voltage decay 350 across the antenna 132 after the pulse 349. The downhole controller 110 performs a Fast Fourier Transform (FFT) of the voltage decay 350 to derive a spectral composition of the decay 350, a composition that provides the resonant frequency 352 of the antenna 132, as depicted in FIG. 13. Then downhole controller 110 determines a difference between the determined resonance frequency and the Larmor frequency and makes corresponding corrections by activating the appropriate switches 128 of the resonance tuning circuit 126. In this manner, in some embodiments, after each NMR measurement sequence, the downhole controller 110 repeats the above-described calibration to keep the antenna 132 tuned to a frequency near the Larmor frequency.

Figure 14:
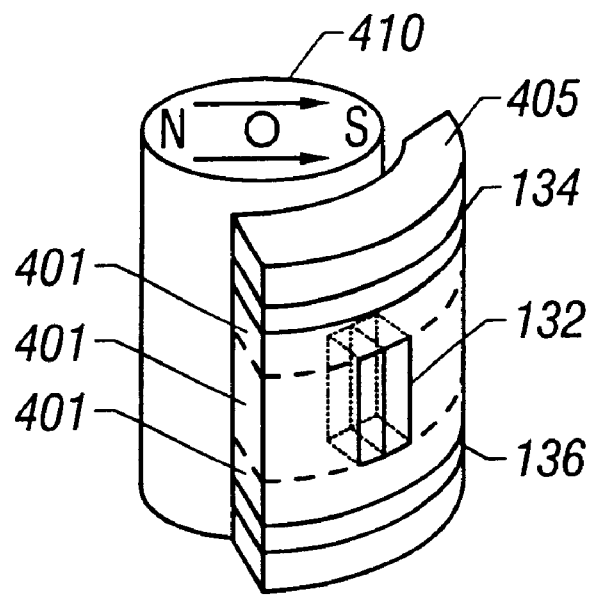
FIG. 14 is a schematic diagram of a sensor of the tool according to an embodiment of the invention.
Figure 15:
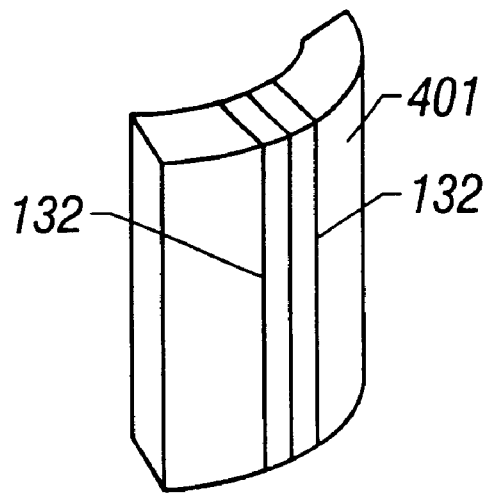
FIG. 15 is a schematic diagram of a portion of the sensor of FIG. 14 according to an embodiment of the invention.

Referring to FIGS. 3 and 14, the NMR sensor 57 includes a cylindrical permanent magnet 410 to establish a static magnetic $B_0$ field for performing the NMR measurement sequence. The magnetic field of the magnet 410 is polarized across the diameter of the magnet 410. The sensor 57 also includes a ferrite material 405 (i.e., a ferromagnetic material) that is located adjacent to and partially circumscribes the permanent magnet 410 about a longitudinal axis of the magnet 410. The antennae 134 and 136 are located near opposite ends of the ferrite material 405 and are formed from corresponding coils that are wound around the ferrite material 405 such that the magnetic moments of the antennae 134 and 136 are parallel to the longitudinal axis of the magnet 410. Unlike the antennae 134 and 136, the antenna 132 is formed from a coil that has a magnetic moment that is tangential to the longitudinal axis of the permanent magnet 410. To accomplish this, the coil that forms the antenna 132 extends around a section 401 of the ferrite material 405, as depicted in FIG. 15. In this manner, the ferrite material 405 may be formed from stacked sections 401.

Figure 16:
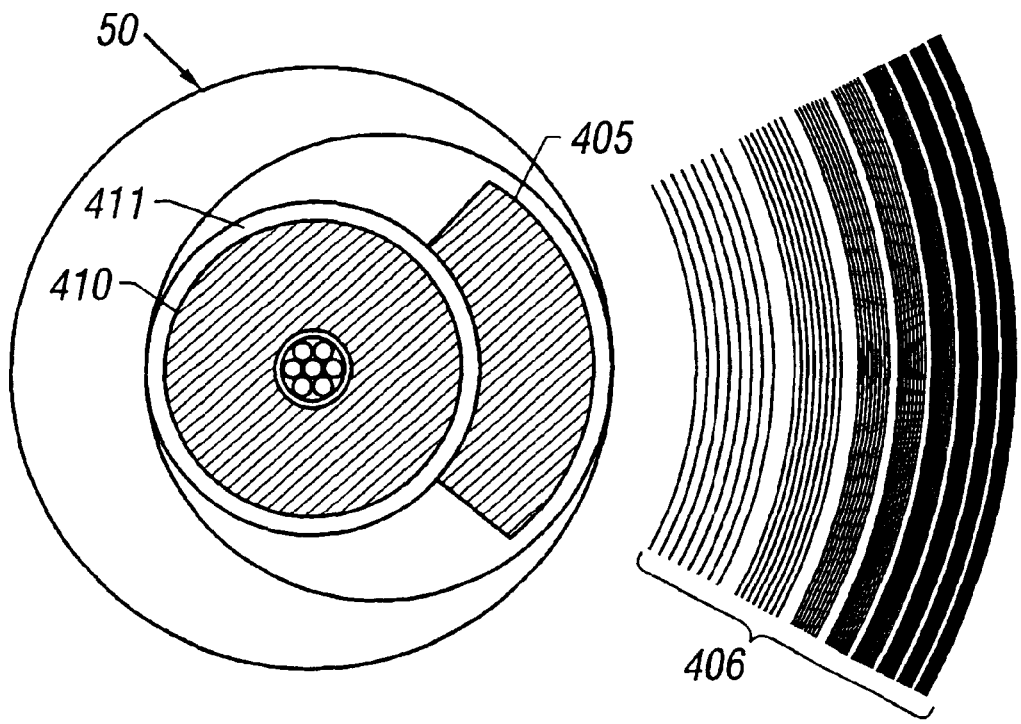
FIG. 16 is a top view of the sensor of FIG. 14 according to an embodiment of the invention.
Figure 17:
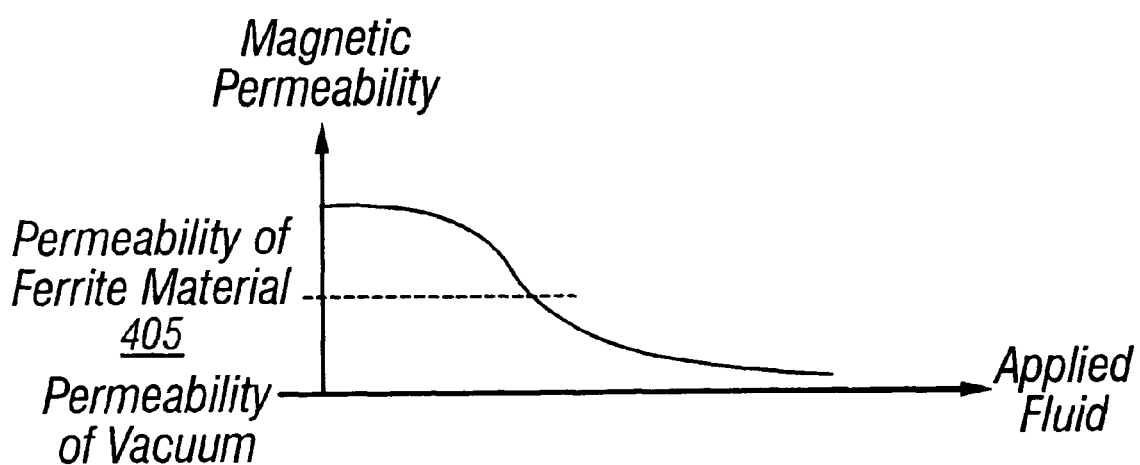
FIG. 17 is a plot a magnetic permeability of a ferromagnetic material of the sensor according to an embodiment of the invention.

The ferrite material 405 aids both the static magnetic field that is created by permanent magnet 410 and the generation/reception of RF signals by the antennae 132, 134 and 136. In this manner, the ferrite material 405 becomes radially polarized, as depicted in FIG. 16, to effectively radially extend the static magnetic field. Referring to FIG. 17, the static magnetic field also raises the magnetic permeability of the ferrite material between a saturated level and the permeability of a vacuum to aid in the reception of spin echo signals and the transmission of RF pulses.

The RF antenna coils of conventional tools may circumscribe the permanent magnet. However, unlike conventional tools, the antennae 132, 134 and 146 are formed around the ferrite material 405. Due to this arrangement, in some embodiments, a metallic cylindrical sleeve 410 (see FIG. 16) encases the permanent magnet 405, an arrangement not possible when the coils circumscribe permanent magnet 405. The sleeve 410 protects and provides structural support to prevent the permanent magnet 405 from shattering when the tool 50 is retrieved uphole.

Figure 18:
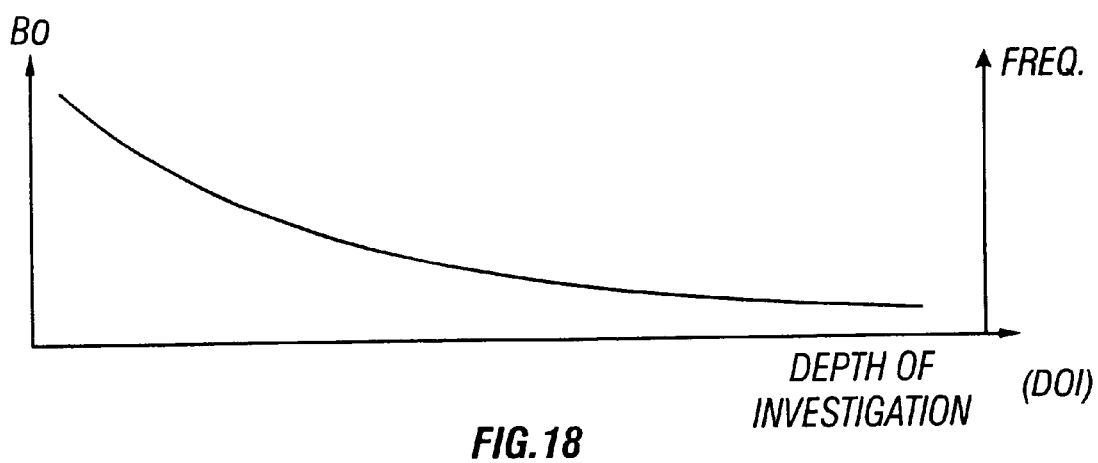
FIG. 18 is a plot illustrating the relationships between the frequency of transmission pulses and the static magnetic field versus the depth of investigation.

The region of the formation that is investigated by the NMR measurement is determined by the condition:

$$|\omega - \gamma B_0| < B_1,$$

where $\omega$ is the center frequency of the RF pulses, $\gamma$ is the gyromagnetic ratio, which is $(2\pi).(4258)$ radian/sec/Gauss for protons; $B_0$ is the magnitude of the static magnetic field; and $B_1$ is the magnitude of the component of the RF field that is perpendicular to the static field. The magnitudes of these fields are position dependent. The region in which the resonance condition is satisfied is shaped like a thin shell. The thickness of the resonant shell is on the order of 1 mm. The distance from the logging tool to the resonant shell is controlled by the frequency of the RF pulses as described in U.S. Pat. No. 3,597,681, entitled, "Nuclear Magnetic Well Logging," issued on Aug. 3, 1971. FIG. 18 shows that the magnitude of the static field is a decreasing function of the distance from the logging tool. Therefore, decreasing the frequency of the RF pulses causes the tool to investigate deeper into the formation. One of the functions of the programmable pulse sequencer 111 is to set the frequency synthesizer 116 to produce a particular frequency that corresponds to a predetermined depth into the formation. The pulse sequencer 111 can rapidly change the frequency of the synthesizer 116, thereby changing the depth of investigation.

What is claimed is:

1. An NMR measurement apparatus comprising:
   a permanent magnet;
   a ferromagnetic material located adjacent to the permanent magnet;
   at least one coil circumscribing the ferromagnetic material; and
   a circuit coupled to the coil and adapted to use said at least one coil and the permanent magnet to perform NMR measurements.

2. The NMR measurement apparatus of claim 1, wherein the permanent magnet comprises a cylindrical magnet having a longitudinal axis and the ferromagnetic material at least partially circumscribes the permanent magnet about the longitudinal axis of the cylindrical magnet.

3. The NMR measurement apparatus of claim 2, wherein the magnet produces a magnetic field in an earth formation and the coil produces a radio frequency field orthogonal to the magnetic field in the earth formation.

4. The NMR measurement apparatus of claim 3, wherein the magnetic is polarized across the diameter of the magnet.

5. The NMR measurement apparatus of claim 4, wherein the magnet has a magnetization direction polarized in a direction pointing away from the ferromagnetic material.

6. The NMR measurement apparatus of claim 4, wherein the magnet has a magnetization direction polarized in a direction pointing toward the ferromagnetic material.

7. The NMR measurement apparatus of claim 4, wherein the magnet produces a magnetic filed along a longitudinal axis of the NMR measurement apparatus.

8. The NMR measurement apparatus of claim 4, wherein the magnet has a magnetization direction polarized in a direction pointing adjacent the ferromagnetic material.

9. The NMR measurement apparatus of claim 4, wherein the magnet produces a magnetic field tangential to the NMR measurement apparatus.

10. The NMR measurement apparatus of claim 1, wherein the permanent magnet substantially influences the magnetic permeability of the ferromagnetic material.

11. The NMR measurement apparatus of claim 1, wherein the permanent magnetic establishes a static magnetic field and the ferromagnetic material substantially influences the static magnetic field.

12. The NMR measurement apparatus of claim 1, wherein the coil circumscribes the ferromagnetic material about the transverse axis of the ferromagnetic material.

13. The NMR measurement apparatus of claim 12, wherein the coil comprises a first cross coil and a second cross coil, the first coil and the second coil located proximate opposite ends of the ferromagnetic material.

14. The NMR measurement apparatus of claim 12, further comprising:
a second coil circumscribing the ferromagnetic material about a longitudinal axis of the ferromagnetic material.

15. The NMR measurement apparatus of claim 14, wherein the second coil circumscribes the ferromagnetic material about a transverse axis of the ferromagnetic material.

16. The NMR measurement apparatus of claim 14, wherein the second coil circumscribes the ferromagnetic material such that a magnetic moment of the second coil is parallel to a longitudinal axis of the magnet.

17. The NMR measurement apparatus of claim 1, wherein the coil circumscribes the ferromagnetic material such that a magnetic moment of the coil is parallel to the longitudinal axis of the magnet.

18. The NMR measurement apparatus of claim 1, wherein the coil circumscribes multiple sides of the ferromagnetic material.

19. An NMR measurement apparatus comprising:
a permanent magnet;
a metallic housing at least partially encasing the permanent magnet;
a ferromagnetic material located outside the metallic housing and adjacent the permanent magnet;
at least one coil located outside of the housing; and
a circuit coupled to the coil and adapted to use said at least one coil and the permanent magnet to perform NMR measurements.

20. The NMR measurement apparatus of claim 19, further comprising:
a ferromagnetic material circumscribed by said at least one coil.

21. The NMR measurement apparatus of claim 20, wherein the coil circumscribes the ferromagnetic material about a transverse axis of the ferromagnetic material.

22. The NMR measurement apparatus of claim 21, wherein the coil comprises a first cross coil and a second cross coil, the first cross coil and the second cross coil are located proximate opposite ends of the ferromagnetic material.

23. The NMR measurement apparatus of claim 21 further comprising:
a second coil circumscribing the ferromagnetic material about the longitudinal axis of the ferromagnetic material.

24. The NMR measurement apparatus of claim 23, wherein the second coil circumscribes the ferromagnetic material about the transverse axis of the ferromagnetic material.

25. The NMR measurement apparatus of claim 23, wherein the coil circumscribes the ferromagnetic material such that the magnetic moment of the coil is parallel to the longitudinal axis of the magnet.

26. The NMR measurement apparatus of claim 20, wherein the coil circumscribes the ferromagnetic material such that a magnetic moment of the coil is parallel to the longitudinal axis of the magnet.

27. The NMR measurement apparatus of claim 20, wherein the magnet produces a magnetic field in an earth formation and the coil produces a radio frequency field orthogonal to the magnetic field in the earth formation.

28. The NMR measurement apparatus of claim 27, wherein the magnet is polarized across the diameter of the magnet.

29. The NMR measurement apparatus of claim 27, wherein the magnet has a magnetization direction polarized in a direction pointing away from the ferromagnetic material.

30. The NMR measurement apparatus of claim 27, wherein the magnet has a magnetization direction polarized in a direction pointing toward the ferromagnetic material.

31. The NMR measurement apparatus of claim 27, wherein the magnet produces a magnetic filed along a longitudinal axis of the NMR measurement apparatus.

32. The NMR measurement apparatus of claim 27, wherein the magnet has a magnetization direction polarized in a direction pointing adjacent the ferromagnetic material.

33. The NMR measurement apparatus of claim 27, wherein the magnet produces a magnetic field tangential to the NMR measurement apparatus.

34. The NMR measurement apparatus of claim 20, wherein the coil circumscribes multiple sides of the ferromagnetic material.

35. The NMR measurement apparatus of claim 20, wherein the permanent magnet comprises a cylindrical magnet having a longitudinal axis and the ferromagnetic material at least partially circumscribes the permanent magnet about the longitudinal axis of the cylindrical magnet.

36. The NMR measurement apparatus of claim 19, further comprising:
a ferromagnetic material located near the metallic housing.

* * * * *